(12) United States Patent
Li et al.

(10) Patent No.: US 10,595,135 B2
(45) Date of Patent: Mar. 17, 2020

(54) HEARING EVALUATION AND CONFIGURATION OF A HEARING ASSISTANCE-DEVICE

(71) Applicant: Concha Inc., San Carlos, CA (US)

(72) Inventors: Amy Li, San Carlos, CA (US);
Matthew Sorg, San Carlos, CA (US);
David Northway, San Carlos, CA (US)

(73) Assignee: Concha Inc., San Carlos, CA (US)

( * ) Notice: Subject to any disclaimer, the term of this patent is extended or adjusted under 35 U.S.C. 154(b) by 0 days.

(21) Appl. No.: 16/383,666

(22) Filed: Apr. 15, 2019

(65) Prior Publication Data

US 2019/0356989 A1    Nov. 21, 2019

Related U.S. Application Data

(60) Provisional application No. 62/657,625, filed on Apr. 13, 2018.

(51) Int. Cl.
*H04R 25/00* (2006.01)
*A61B 5/12* (2006.01)
*A61B 5/00* (2006.01)

(52) U.S. Cl.
CPC ............ *H04R 25/50* (2013.01); *A61B 5/121* (2013.01); *H04R 25/70* (2013.01); *A61B 5/4005* (2013.01); *H04R 25/554* (2013.01); *H04R 2225/41* (2013.01)

(58) Field of Classification Search
CPC ...... H04R 25/50; H04R 25/70; H04R 25/554; H04R 2225/41; A61B 5/121; A61B 5/4005

USPC ........................................................ 381/314
See application file for complete search history.

(56) References Cited

U.S. PATENT DOCUMENTS

| | | | | |
|---|---|---|---|---|
| 8,379,871 | B2* | 2/2013 | Michael | H04R 5/04 381/312 |
| 8,761,421 | B2* | 6/2014 | Apfel | H04R 25/70 381/313 |
| 9,020,621 | B1* | 4/2015 | Proctor | H04R 5/04 700/94 |
| 9,344,815 | B2* | 5/2016 | Selig | H04R 25/50 |
| 2010/0232613 | A1* | 9/2010 | Krause | A61N 1/08 381/60 |
| 2011/0100127 | A1* | 5/2011 | Beck | A61B 5/121 73/585 |

(Continued)

*Primary Examiner* — Sean H Nguyen
(74) *Attorney, Agent, or Firm* — Run8 Patent Group, LLC; Peter Miller

(57) ABSTRACT

A method for evaluating hearing of a user comprising: generating a baseline hearing profile for the user comprising a set of gain values based on a volume setting, each gain value in the set of gain values corresponding to a frequency band in a set of frequency bands; accessing a soundbite comprising a phrase characterized by a frequency spectrum predominantly within one frequency band; playing the soundbite amplified by a first gain in the frequency band; playing the soundbite amplified by a second gain in the frequency band; receiving a preference input representing a preference of the user from amongst the soundbite amplified by the first gain and the soundbite amplified by the second; and modifying a gain value, corresponding to the frequency band, in the baseline hearing profile based on the preference input to generate a refined hearing profile compensating for hearing deficiency of the user.

20 Claims, 4 Drawing Sheets

(56) References Cited

U.S. PATENT DOCUMENTS

| | | | | |
|---|---|---|---|---|
| 2013/0266165 A1* | 10/2013 | Neumeyer | ............ | H04R 25/30 381/314 |
| 2015/0023512 A1* | 1/2015 | Shennib | ................ | H04R 25/70 381/60 |
| 2015/0023535 A1* | 1/2015 | Shennib | ................ | H04R 25/70 381/314 |
| 2019/0231233 A1* | 8/2019 | Turner | ................ | A61B 5/0022 |

* cited by examiner

HEARING EVALUATION AND CONFIGURATION OF A HEARING ASSISTANCE-DEVICE

CROSS-REFERENCE TO RELATED APPLICATIONS

This application claims the benefit of U.S. Provisional Application No. 62/657,625, filed on 13 Apr. 2018, which is incorporated in its entirety by this reference.

TECHNICAL FIELD

This invention relates generally to the field of sound augmentation devices and hearables and specifically to a new and useful method for assessing hearing and configuring a hearing-assistance device in the field of sound augmentation devices and hearables.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figures 1, 2:
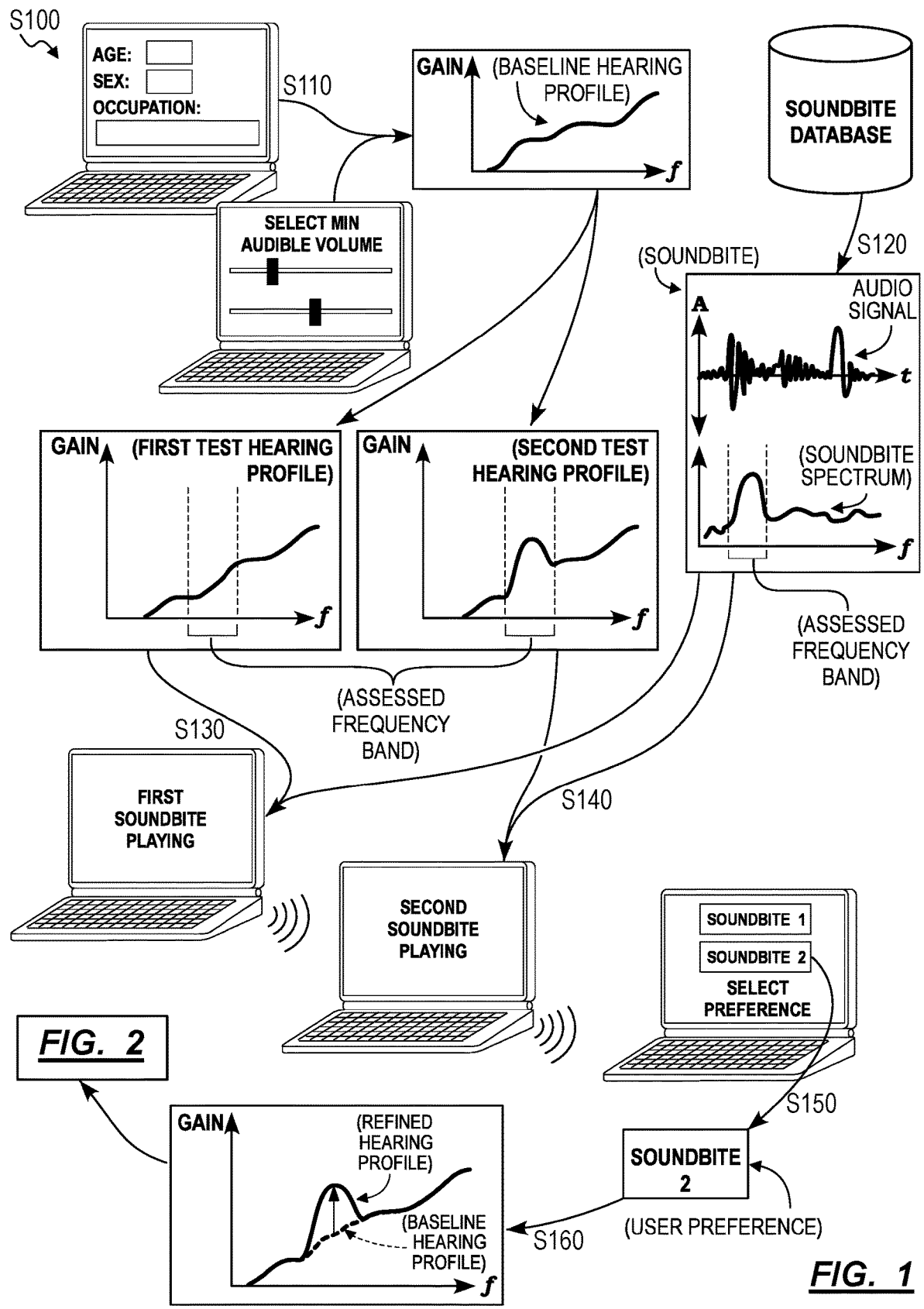
FIG. 1 is a flowchart representation of a method.
FIG. 2 is a flowchart representation of a variation of the method.
Figure 2:
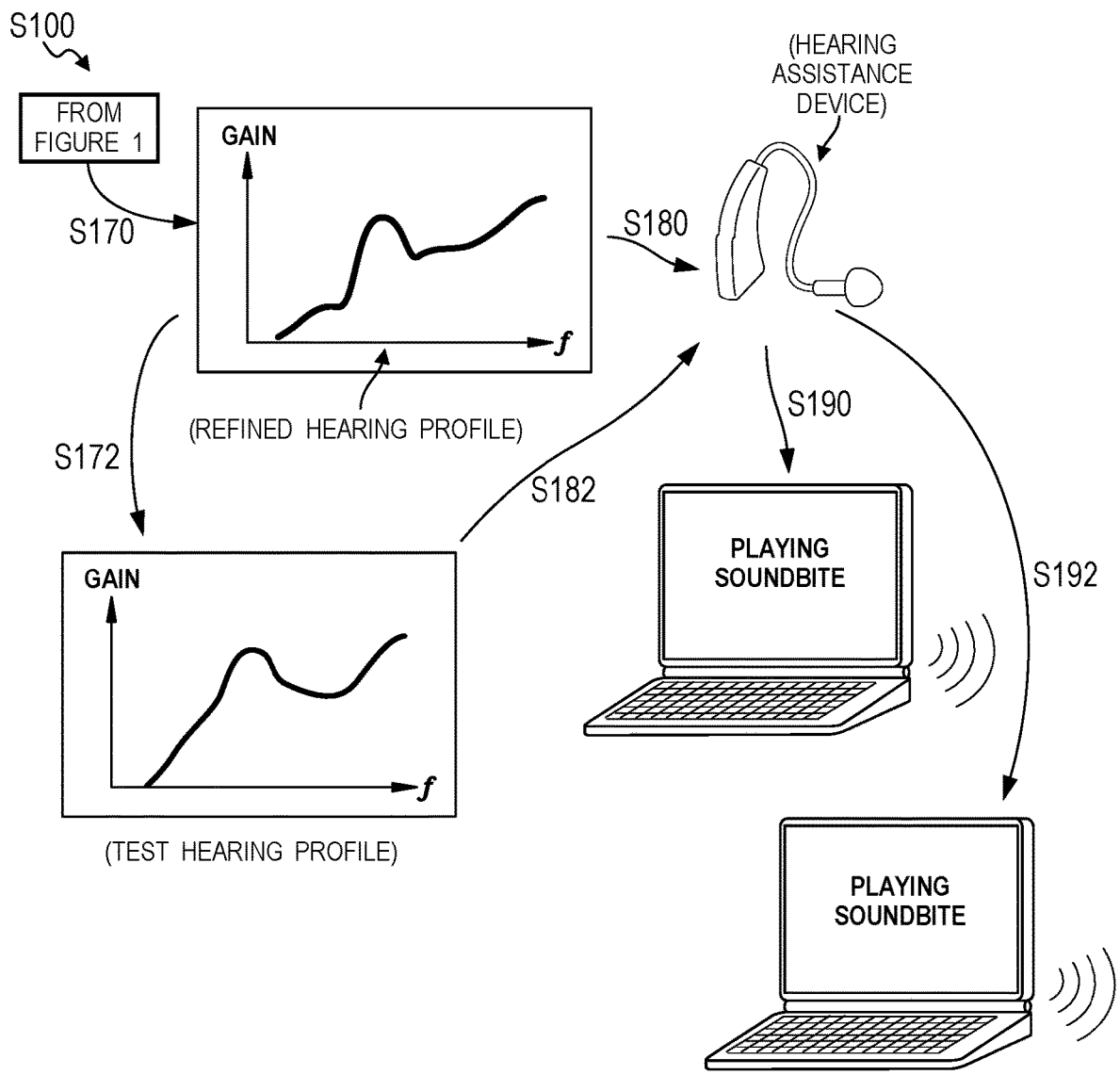
Figure 2:
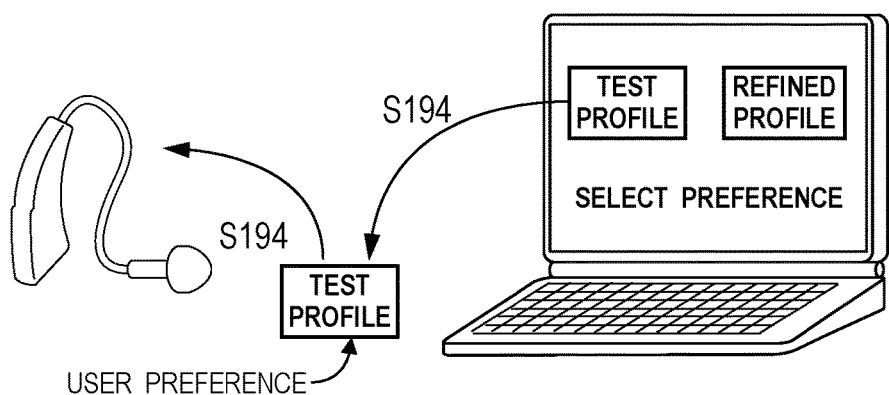

As shown in FIG. 1, a method S100 for evaluating hearing of a user can include: generating a baseline hearing profile for the user comprising a set of gain values based on a first volume setting, each gain value in the set of gain values corresponding to a frequency band in a set of frequency bands spanning a human-audible frequency range in Block S110; accessing a first soundbite comprising a first spoken phrase characterized by a first frequency spectrum predominantly within a first frequency band in the set of frequency bands in Block S120; playing the first soundbite amplified by a first gain in the first frequency band in Block S130; playing the first soundbite amplified by a second gain in the first frequency band different from the first gain in Block S140; receiving a first preference input representing a preference of the user from amongst the first soundbite amplified by the first gain in the first frequency band and the first soundbite amplified by the second gain in the first frequency band in Block S150; and modifying a first gain value, corresponding to the first frequency band, in the baseline hearing profile based on the first preference input to generate a first refined hearing profile compensating for hearing deficiency of the user in Block S160.

As shown in FIG. 2, one variation of the method S100 can include: accessing a first hearing profile for a user comprising a first set of gain values, each gain value in the first set of gain values corresponding to a frequency band in a set of frequency bands spanning human audible range and characterized by a first gain value in the first set of gain values corresponding to a first frequency band in Block S170; uploading the first hearing profile to the hearing assistance device of the user in Block S180; at a first time, and in response to receiving a confirmation of activation of the first hearing profile from the hearing assistance device, playing a first soundbite comprising a first spoken phrase characterized by a first frequency spectrum predominantly within the first frequency band in Block S190; accessing a second hearing profile for the user comprising a second set of gain values, each gain value in the second set of gain values corresponding to a frequency band in the set of frequency bands and characterized by a second gain value in the second set of gain values corresponding to a first frequency band in Block S172; uploading the second hearing profile to the hearing assistance device in Block S182; at a second time succeeding the first time and in response to receiving a confirmation of activation of the second hearing profile from the hearing assistance device, replaying the first soundbite in Block S192; in response to receiving a first preference input representing a preference of the user for the second hearing profile, selecting the second hearing profile in Block S194; and prompting the hearing assistance device to set the second hearing profile as an active hearing profile for the hearing assistance device in Block S196.

2. Applications

Generally, the method S100 is executed by a system (e.g., a mobile computing device executing an application, a computer system, and/or a distributed computer network) to evaluate a user's hearing deficiency (i.e. an inability to hear soft sounds, a sensitivity to loud sounds, or any other hearing challenge) and to configure a hearing-assistance device to amplify and/or attenuate incoming sound to compensate for the user's hearing deficiency and to enable the user to better perceive and comprehend human speech (and any other sound) in various environments (not just in a quiet room). More specifically, the system can execute the method S100 to: generate a baseline hearing profile approximately compensating for hearing deficiency of the user based on user's demographic data and an initial hearing test; collecting hearing preferences from the user (e.g., in the form of volume adjustments) while playing a series of soundbites including spoken (e.g., vocal) phrases, each soundbite characterized by spectral peaks within particular frequency bands; refining the baseline hearing profile to better reflect the user's hearing ability across the audible spectrum based on these hearing preferences; upload the refined hearing profile to a hearing assistance device; and further refine amplification settings of the hearing assistance device to compensate for the hearing deficiency of the user. Thus, the system can interface with a user to generate an improved hearing profile that better compensates for frequency-specific hearing deficiency in the context of language comprehension when compared to standard audiograms and without the need to visit an audiologist. Furthermore, the system can fine tune the hearing profile according to the user's specific hearing assistance device.

The system executes Blocks of the method S100 utilizing a combination of a microphone, a digital signal processor (e.g., within a personal, computer, laptop, smartphone), and a speaker (e.g., headphones, internal speakers of the signal processing device). Additionally or alternatively, the system interfaces (e.g., via wireless protocols such as BLUETOOTH or BLUETOOTH LOW ENERGY) with a hearing assistance device to execute Blocks of the method S100. As used herein, a "hearing assistance device" can include a hearing aid, a wearable hearing-related device (a "hearable" device), earphones/headphones in coordination with an integrated microphone, or any other device capable of augmenting incoming sound.

Generally, a "hearing profile" as used herein, refers to an array, matrix, or discrete function that relates a specific gain (i.e. relative volume amplification) to each frequency band within a set of frequency bands spanning the human audible range of frequency (e.g., 20 to 20,000 Hz). Therefore, the system can selectively and differentially amplify and/or attenuate various frequency bands in a given soundbite according to a hearing profile. Furthermore, the system can communicate with a hearing assistance device to configure the hearing assistance device with various hearing profiles in order to execute Blocks of the method S100. Additionally, a hearing profile can also relate the output gain to other characteristics of a given soundbite such as the volume (i.e. intensity) of the soundbite in each frequency band, thereby adjusting the output volume according to different input volumes measured within each frequency band or for the overall volume/intensity of the soundbite.

As shown in FIG. 1, the system can generate a baseline hearing profile that roughly (approximately) compensates for the hearing deficiency of the user according to an initial hearing assessment (e.g., a simplified audiogram) of the user and demographic data input by the user (e.g., age, sex, and/or occupation). For example, the system can render a set of data input fields within a user portal (e.g., a graphic user interface) in order to record demographic data associated with the user. Additionally, the system can render one or more slider bars (or any other adjustable user-interface element) with which the user may indicate the lowest audible volume of a testing tone (e.g., a 5 kHz tone) or the lowest volume at which the user can understand speech concentrated within a particular frequency band. The system can then estimate (e.g., via machine learning or other statistical techniques) a baseline hearing profile for the user.

After generating the baseline hearing profile for the user, the system can further refine the baseline hearing profile to generate a refined hearing profile for the user and to fully characterize the hearing deficiency of the user (e.g., in order to recommend particular hearing assistance device) by performing a hearing assessment of the user. The hearing assessment can include a series of soundbites (e.g., sentences including phonemes having specific frequency characteristics) that are selectively output by the computing device, such as through headphones connected to or paired with the computing device. During this hearing assessment, the system can select a soundbite (i.e. a reproduceable audio signal) with a frequency spectrum predominantly within a particular frequency band. The system can then apply the baseline hearing profile to the soundbite and play the soundbite for the user. Subsequently the system can play the soundbite a second time with altered gain within the particular frequency band (e.g., by altering the baseline hearing profile within the particular frequency band such as in an A/B testing procedure). After listening to the soundbite repeated according to the altered hearing profile within the frequency band, the user can then form a preference as to which of the soundbites was clearer or more easily perceived by the user.

The system can then request qualitative feedback from the user regarding how well the user has comprehended each version of the soundbite. If the system detects that the user has expressed a preference for the modified hearing profile, then the system can modify the hearing profile of the user accordingly thereby providing an improved characterization of the user's hearing deficiency (e.g., as expressed by the hearing profile of the user).

The system can perform the above hearing assessment multiple times for the same frequency band (e.g., by playing a pair of soundbites with various gain values applied within the frequency band) in order to refine the user's hearing deficiency and preferred gain within that frequency band. Furthermore, the system can perform the hearing assessment across multiple frequency bands included in the hearing profile in order to precisely determine the user's hearing preferences.

The system can compile the user's feedback from the hearing assessment tests into a refined hearing profile that, when applied to an input audio signal, enhances (amplifies and/or reduces) select frequencies (at different input volumes) within the audible or vocal spectrum to compensate for the user's hearing deficiency, thereby enabling the user to better hear sound generally and to comprehend human speech more specifically. In particular, the system can generate and store the refined hearing profile executable by an audio device to amplify select frequencies and thus enable the user to better comprehend human speech given feedback collected from the user during a brief hearing assessment.

Upon receipt of a hearing assistance device, the user can pair the hearing assistance device with the system, and the system can upload the refined hearing profile—generated during the hearing assessment—onto the hearing assistance device, such as via an ad hoc local wireless network or according to a short range wireless communication protocol. Because the output frequency response of the hearing assistance device may differ from system's frequency response (e.g., the speakers or headphones connected to the computational device), the system can commence an on-device hearing assessment, now with the hearing assistance device. During the on-device hearing assessment, the system can play back select soundbites—with original and/or modified amplitudes of select frequencies—to the hearing assistance device; and the hearing assistance device can output these modified soundbites, further modified according to the baseline hearing profile currently loaded onto the hearing assistance device, for the user. For example, during the on-device hearing assessment, the hearing assistance device can: upload the refined hearing profile to the hearing assistance device; play a soundbite (e.g., including a spoken phrase) to be amplified locally by the hearing assistance device according to the refined hearing profile; upload a modified version of the refined hearing profile to the hearing assistance device; replay the soundbite; and receive an indication of the user's preference in order to generate a revised hearing profile. The system can then: prompt the user to select which version of the refined hearing profile she prefers; derive a hearing preference and/or hearing ability of the user from the user's feedback; generate a revised hearing profile for the user's hearing assistance device; and upload this revised hearing profile to the hearing assistance device for implementation by the hearing assistance device.

The system and the hearing assistance device can cooperate to repeat this process during the on-device hearing assessment and/or throughout many hearing assessments with the user over time in order to converge on a hearing profile that, when executed by the hearing assistance device, amplifies an input audio signal into an output audio signal that is more audible to the user.

Furthermore, the system can implement Blocks of the method S100 to enable the user to adjust sound amplification output by the hearing assistance device in order to attenuate environmental and/or other background noise and to selectively augment particular frequencies that may better enable the user to comprehend speech in the presence of background noise. For example, in a loud restaurant, the user may experience difficulty hearing a voice of a friend due to ambient music, voices, and other noises. In this example, the system can implement methods described above to present a hearing assessment to the user and to adjust the hearing profile executed by the hearing assistance device in real-time in order to: decrease specific gain settings at frequency bands corresponding to background noise and increase specific gain settings at frequency bands corresponding to the voice of the friend.

The system can therefore implement Blocks of the method S100 to streamline: identification of a user who may benefit from a hearing assistance device; initial configuration of a hearing assistance device to output a hearing profile matched to the user's hearing abilities and preferences; and revision and improvement of the hearing profile for the user's hearing assistance device over time. The system can thus enable users with hearing deficiency (e.g., mild or moderate hearing deficiency) to access and configure their own hearing assistance device. By enabling such a user to locally assess her own hearing at her own computing device and to adjust amplification of select audio frequencies by her hearing assistance device, the system may also enable the user to quickly improve her speech comprehension (e.g., on the fly), tailor her hearing assistance device to her immediate and long-term needs, and avoid visiting an audiologist or other auditory specialist each time the user desires adjustment to her hearing assistance device. In particular, the system can enable the user to complete a self-assessment of her hearing and to leverage results of this self-assessment to tune her own hearing assistance device to her needs over time.

The term "amplify" as used herein indicates an augmentation of an audio signal according to a particular gain. Therefore amplification can result in an actual increase in volume of an audio signal or an attenuation of an audio signal depending on the particular gain.

3. System

As described above, the system can include a distributed network of computing devices and/or computer systems that cooperate to assess a user's hearing, generate hearing profiles representing frequencies at which the user desires amplification in order to better comprehend speech, such as during conversation. For example, the system can include a remote computer system that renders a user portal, which is then made accessible to a local computing device, such as a smartphone or tablet computer, through a web browser or application executing on a local computing device. The system can therefore enable a user to initiate a hearing assessment, listen to various original and/or modified soundbites, and enter responses to prompts related to her preferences for these soundbites via the user portal, and the system can also log these responses within a user profile assigned to the user (e.g., in a remote database). The system can then generate and revise a hearing profile for the user based on these responses.

Additionally, the system can connect (e.g., via a wired or wireless connection) with sound generating devices, such as speakers, headphones or earphones, to audibly reproduce various amplified versions of soundbites, tones, or any other audio for evaluation by the user. Additionally, the system can interface with noise-cancelling headphones or any other noise-cancelling device to reduce or eliminate ambient noise during hearing assessments.

The system can also interface or communicate with a hearing aid (i.e. a pair of independent or linked hearing aids) or other hearing assistance device configured to amplify frequencies of sounds according to the hearing profile generated for the user. Generally, the hearing aid or hearing assistance device can include a microphone configured to detect audible signals, such as speech, music, and/or other sound. The hearing aid can also include: a controller or signal processor configured to amplify select frequency bands of input audible signals detected by the microphone according to a hearing profile currently loaded onto the hearing aid (e.g., a left hearing profile for a left hearing aid configured to engage the user's left ear; a right hearing profile for a right hearing aid configured to engage the user's right ear); and a speaker configured to output these modified audio signals. The hearing aid or hearing assistance device can further include a wireless communication module configured to wirelessly connect to the user's computing device and to download baseline, refined, and/or revised hearing profiles from the computing device.

However, the system can include any other local or remote hardware or software elements configured to execute Blocks of the method S100 in order to compensate for the user's hearing deficiency and improve the user's speech comprehension. For example, a microphone can be inserted inside the ear canal to record the actual sound output by the hearing aid's speaker. In this example, the microphone can record how the actual sound reverberates within the ear canal of the user and transform the sound amplification profile, which is output by the hearing aid's speaker, to compensate for distortion and/or other deviation of the actual sound recorded by the microphone from the sound amplification profile.

4. Hearing Profiles

Generally, the system executes the method S100 in order to identify a compensatory hearing profile for a user with hearing deficiency, thereby substantially improving the user's audio perception and, specifically, the user's speech comprehension. Thus, the system generates and maintains various hearing profiles that each define a frequency response for a hearing assistance device (across the full frequency range of human audio perception). Therefore, when the system uploads a hearing profile for a hearing assistance device, the hearing assistance device can implement the hearing profile, via electronic amplifiers and/or a digital signal processor within the hearing assistance device, to replicate the frequency response defined by the uploaded hearing profile, thereby compensating for the user's hearing deficiency. Furthermore, the system can apply the hearing profile to its own audio outputs, such as by modifying a stored or streamed audio signal according to the frequency response indicated by a hearing profile (such as by applying the hearing profile to stored soundbites or live telephone audio). As a result, the system can output an audio signal that is amplified such that the audio signal can be better perceived and/or comprehended by the user or such that the system can test the user's perception and/or comprehension of the output audio (such as during the hearing assessment process further described below) in order to further improve the estimated compensatory hearing profile for the user.

As briefly described above, the system can define a hearing profile in a number of different ways depending on the implementation. In one implementation, the system can define a hearing profile as an array of gain values, wherein each gain value corresponds to a particular frequency band in the human-audible frequency range. Alternatively, the system can define a hearing profile as a matrix of gain value, wherein each gain value in the matrix of gain values corresponds to a frequency band in the human-audible frequency range and a spectral density of the input audio signal within that frequency band. Thus, in this implementation, the hearing profile can indicate a different frequency response within a given frequency band corresponding to a different input intensity for that frequency band. Additionally, the hearing profile can indicate a different frequency response depending on the overall intensity of the input audio signal. In yet another implementation, the system can define the hearing profile as a continuous or discrete frequency response function with a range corresponding to the human-audible frequency range.

Furthermore, the system can define a separate hearing profile for each ear of the user (e.g., a right hearing profile and a left hearing profile) in order to compensate for hearing deficiency differences between the user's ears.

4.1 Frequency Bands

In one implementation, the system generates hearing profiles that indicate a gain value for each of a predetermined set of frequency bands spanning a human-audible frequency range. For example, the system can define a hearing profile including a gain value corresponding to 500-1000 Hz, 1000-1500 Hz, 1500-2000 Hz, 2000-3000 Hz, 3000-4000 Hz, 4000-6000 Hz, and 6000-8000 Hz. Alternatively, the system can define hearing profiles for a predetermined set of frequency bands corresponding to particular phonemes of human speech. For example, the set of frequency bands can include several vowel formants, sonorant consonant formants, and a set of consonant frequency bands each consonant frequency band, wherein each consonant frequency band includes the spectral range corresponding to a set of consonants grouped by typical frequency content of the consonants.

In one implementation, the system can define hearing profiles according to frequency bands of variable resolution based on the hearing assistance device available to the user or based on the demographic data of the user. For example, the system can offer higher resolution (or a larger number of smaller frequency bands) for users with hearing deficiency caused by overexposure to specific frequencies. Furthermore, the system can adjust the number, bandwidth, and or center frequency of any frequency band based on the results of the hearing assessment process further described below.

4.2 Hearing Profile Terminology

As the system executes Blocks of the method S100, the system generates different hearing profiles (or sound profiles) that converge on a hearing profile that can compensate for the particular hearing deficiency of the user given a particular hearing assistance device. In Block S110, the system generates a "baseline hearing profile" for the user. The baseline hearing profile indicates an initial estimate hearing profile that approximately compensates for a user's hearing deficiency. However, the baseline hearing profile is further refined and revised in subsequent Blocks of the method S100.

In Blocks S130 and S140, the system can generate soundbites amplified according to "test hearing profiles." The test hearing profiles are based on the baseline hearing profile, however, each test hearing profile includes a modified gain value in at least one frequency band (e.g., the frequency band currently being tested in the hearing assessment process). For example, in Blocks S130 and S140, the system can generate two test hearing profiles in order to receive a user's preference regarding the gain value of a particular frequency band. In this example, the first test hearing profile can include a first gain value corresponding to the particular frequency band that is higher than the gain value of the baseline hearing profile for the same frequency band, while the second test hearing profile can include a second gain value that is lower than the gain value of the baseline hearing profile for the same frequency band.

In Block S160, the system generates a "refined hearing profile" according to the results of the hearing assessment process. The refined hearing profile is a modified or derived version of the baseline hearing profile that the system modifies according to the user's expressed preferences for various test hearing profiles presented to the user during the hearing assessment process, as further described below with respect to Block S140.

In Block S196, the system generates and/or uploads a "revised hearing profile" to a hearing assistance device according to the results of the on-device hearing assessment process. The revised hearing profile can be a further refined version of the refined hearing profile that the system modifies according to the particular frequency response characteristics of the user's hearings assistance device.

Thus, by generating, modifying, and testing various hearing profiles according to Blocks of the method S100, the system can select a hearing profile that precisely compensates for the hearing deficiency of the user given the hearing assistance device of the user.

5. Baseline Hearing Profile Estimation

In Block S110 of the method S100, the system generates a baseline hearing profile for the user including a set of gain values based on a first volume setting, each gain value in the set of gain values corresponding to a frequency band in a set of frequency bands spanning human-audible frequency range. More specifically, the system can estimate the hearing deficiency (and a corresponding compensatory hearing profile) of the user based on a set of simplified audiogram tests and/or user provided demographic data. By estimating the baseline profile before further refining and revising the hearing profile of the user via the hearing assessment process further described below, the system can provide a starting point from which to initiate the hearing assessment process, thereby reducing the duration and improving the accuracy of the hearing assessment process.

5.1 Demographic Data

In one implementation, the system can prompt the user to enter demographic information (e.g., age, race, gender, or weight) and/or survey the user about environments, words, and/or particular frequencies which the user struggles to hear. In this variation, the system can access a library of hearing deficiency profiles representing common hearing deficiency types, such as low-frequency hearing deficiency, cookie bite hearing deficiency, and/or noise-induced hearing deficiency. (Each hearing deficiency profile in the library of hearing deficiency profiles can be represented as an audiogram that describes an approximate minimum volume—in decibels—a user can hear at particular frequencies across a frequency spectrum audible to a human.) Based on demographic information and/or survey results provided by the user, the system can estimate a type of hearing deficiency of the user (e.g., noise-induced hearing deficiency). The system can then: access a generic hearing deficiency profile associated with the type of the user's hearing deficiency; and access or generate a generic hearing profile corresponding to the generic hearing deficiency profile accordingly. In particular, the generic hearing profile can be configured to amplify select frequencies for which humans—with the type of hearing deficiency characteristic of the user's demographic—commonly experience hearing deficiency.

Additionally or alternatively, the system can present a subset of generic hearing profiles—such as low-frequency hearing deficiency, noise-induced hearing deficiency, and cookie-bite hearing deficiency—to the user (e.g., through the user portal). The system can then prompt the user to select one of the generic hearing profiles. The computing device can then modify the first soundbite described above according to this selected generic hearing profile to generate the soundbites to be played back to the user during the hearing assessment.

By replaying a sample soundbite both in original form and modified, according to a chosen generic hearing profile in quick succession, the system can enable the user to identify which generic hearing profile she prefers. Upon receipt of the user's preference, the system can then determine whether the generic hearing profile compensates for the user's hearing deficiencies and, if so, the system can set the user's preferred generic hearing profile as the baseline hearing profile in the user according to similar methods.

In one implementation, the system prompts the user, via the user portal to provide the user's demographic data including the user's age, gender, and/or occupation and generate a baseline hearing profile for the user based on the demographic data provided by the user and a hearing profile model further described below.

However, the system can prompt the user to provide any demographic information that may be predictive of frequency-specific hearing deficiency.

5.2 Simplified Audiogram Test

Additionally, in Block S110, the system can, via the user portal, administer a simplified audiogram test in order to estimate a baseline hearing profile for the user. Therefore, the system can prompt the user to specify, via the user portal, a volume setting corresponding to the user's minimum audible volume of a tone of a particular frequency or the user's minimum understandable volume of an exploratory soundbite including speech concentrated within a particular frequency band. Alternatively, the system can prompt the user to specify multiple volume settings each corresponding to a tone or exploratory soundbite within a different frequency band. Once the system receives the user's volume settings, the system can estimate the rest of the user's hearing deficiency according to the received volume settings and generate a baseline hearing profile for the user based on the received volume settings.

In one implementation, the system can render a slider bar (or other similar graphic user interface element), via the user portal, such that, when the user changes the position of the slider bar in the user portal, the system plays the tone or exploratory soundbite at a particular volume based on the position of the slider. Therefore, the user may move the slider until the user can only minimally perceive the tone or understand the speech in the exploratory soundbite. The system can then record the volume setting corresponding to the frequency band corresponding to the tone or exploratory soundbite based on the position of the slider. Thus, the system can: play a tone or exploratory soundbite at an initial volume; prompt the user to adjust the volume from the initial volume to the minimum audible volume to the user; and record the minimum audible volume to the user as a volume setting.

In one implementation, the system prompts the user to specify a minimum audible volume for a set of tones or exploratory soundbites that correspond to frequency bands that are most predictive of the hearing deficiency profile of a user. For example, the system can select a single frequency band that is most correlated with hearing deficiency across a range of frequencies and play a tone or exploratory soundbite corresponding to that frequency band. Alternatively, the system can: receive demographic information from the user; select a set of tones that are most predictive of hearing deficiency in humans with similar demographic characteristics; and render a set of graphical user interface elements prompting the user to provide a minimal audible volume for each of the selected tones. The system can select the tones and/or exploratory soundbites according to conditional logic relating demographic data of the user to predictive tones or exploratory soundbites. Alternatively, the system can select the most predictive tones or exploratory soundbites to play for the user based on a sensitivity analysis on a set of demographic data associated with hearing test data.

Thus, the system can: receive a volume setting, wherein the volume setting represents a minimum audible volume to the user of a tone or exploratory soundbite, the tone or exploratory soundbite characterized by concentration within a frequency band; and generate the baseline hearing profile based on the first volume setting and a hearing profile model, further described below.

Furthermore, the system can generate the baseline hearing profile according to a second volume setting, wherein the second volume setting represents a minimum audible volume to the user or a minimum understandable volume to the user of a second tone or exploratory soundbite, the second tone characterized by a second frequency different from the first frequency; and generate the baseline hearing profile based on the volume setting, the second volume setting, and the hearing model, further described below.

In another implementation, the system can play an exploratory soundbite including speech that predominantly comprises phonemes exhibiting frequency peaks within a particular frequency band instead of a tone of a frequency within the particular frequency band. Thus, upon adjustment of the slider (or other user interface element) by a user, the system can replay (or continue to play) the exploratory soundbite at a volume corresponding to the position of the slider. Additionally, the system can apply a bandpass filter to the exploratory soundbite in order to restrict the output frequencies of the exploratory soundbite to a particular frequency band for the purpose of the test. Furthermore, the system can prompt the user to indicate the minimum comprehendible volume of the exploratory soundbite (when the exploratory soundbite includes speech) as opposed to the minimum audible volume of a tone.

5.3 Hearing Test Model

In one implementation, in Block S110, the system can apply a hearing test model to generate a baseline hearing profile for the user based on an input vector including a set of demographic characteristics of the user and/or a set of volume settings specified by the user. In one variation, the system trains the hearing test model according to a corpus of hearing test data with associated demographic data. Alternatively, the system can access a pre-trained model that performs the same function.

In order to train a hearing test model for generating a baseline hearing profile for a user, the system can access a corpus of hearing test data associated with demographic data. The system can then train (via supervised learning algorithms) a machine learning model to estimate a gain value for each frequency band within the baseline hearing profile based on a selection of demographic and hearing test inputs. For example, the system can train a hearing test model with inputs including the age and occupation of the user as well as the minimum audible volume within the 2000-3000 Hz frequency band for the user. The model can then output a baseline hearing profile based on the specified inputs. Generally, the system can train a hearing test model with inputs that are most predictive of baseline hearing profiles that accurately compensate for hearing deficiency of the user.

The hearing test model can include various artificial neural networks to estimate the gain values of the baseline hearing profile according to input demographic and hearing test data. Alternatively, the system can define a set of hearing deficiency categories such as low-frequency hearing deficiency, cookie bite hearing deficiency, and/or noise-induced hearing deficiency and utilize a classification algorithm (e.g., a support vector machine, naïve Bayes, regression, decision trees) to select the most likely type of hearing deficiency. The system can select a baseline hearing profile corresponding to the selected type of hearing deficiency. In one implementation, the system can also scale the gain of the baseline hearing profile based on a request volume setting from a simplified audiogram test provided to the user.

The system can also execute machine learning models such as active learning models that can select specific demographic data or hearing test data to request from a user in order to estimate a baseline hearing profile for the user. Thus, the system can execute a hearing test model that selects frequencies for the simplified audiogram tests and selects particular demographic characteristics to request from the user that are most predictive of a compensatory baseline hearing profile for the user.

6. Hearing Assessment Process

Upon estimating a baseline hearing profile for the user, the system, in Blocks S120, S130, S140, and S150, executes a hearing assessment process in order to refine the baseline hearing profile to a refined hearing profile that better compensates for the hearing deficiency of the user. More specifically, the system can execute the hearing assessment process for each frequency band (or a subset of the frequency bands) included in the baseline hearing profile in order to refine the gain value corresponding to each frequency band in the baseline hearing profile. The system executes the hearing assessment process by: accessing or selecting a soundbite that includes informational content within the frequency band being assessed; generating two test hearing profiles that differ from the baseline hearing profile; amplifying the soundbite according to each of the two test hearing profiles; playing the amplified soundbites to the user; prompting the user to provide a preference for one of the two amplified soundbites; and modifying the gain value corresponding to the frequency band according to the preference of the user. Thus, the hearing assessment process includes at least the steps of soundbite selection, test hearing profile generation, soundbite amplification, and hearing profile modification based on received user preference. The system can then preferentially execute the hearing assessment process for each frequency band in the baseline hearing profile.

In one implementation, upon the user opening the user portal within the system (or within a web browser) at her computing device and initiating a hearing assessment, the system can: prompt the user to connect her headphones to the computing device; output a sound (e.g., a music track, tone, or phrase) through the connected headphones; and prompt the user to select a default output volume for the headphones at which the user can generally hear or comprehend this sound. The system can then execute the hearing assessment at this default output volume.

6.1 Soundbites

When executing the hearing assessment process, in Block S120, the system can select and/or access a soundbite including a spoken phrase (e.g., a sentence or sequence of sounded words) characterized by a frequency spectrum predominantly within an assessed frequency band in the set of frequency bands. More specifically, the system can access a soundbite, which can include a synthesized or a recorded audio signal including a spoken phrase, that exhibits significant spectral density within a particular frequency band being assessed in the hearing assessment process. Alternatively, the soundbite can include music, noise, select tones, or recognizable sounds (like a fire truck siren).

Figure 3A:
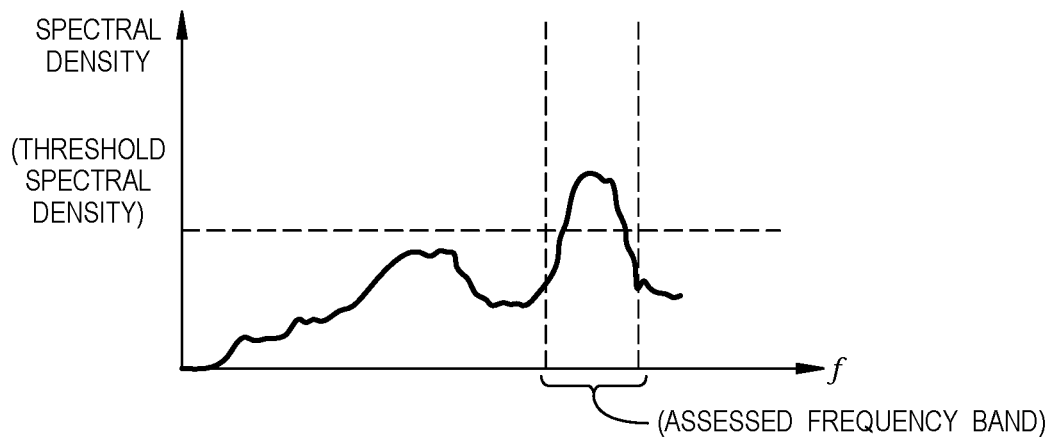
FIGS. 3A, 3B, and 3C are a schematic representations of example soundbites as used in the method.

In one implementation, as shown in FIG. 3A, the system accesses a soundbite characterized by a spectral density within the assessed frequency band exceeding a threshold spectral density. Thus, upon playing the soundbite, the system transmits a greater than threshold amount of the sound energy of the soundbite within the assessed frequency band.

Figure 3B:
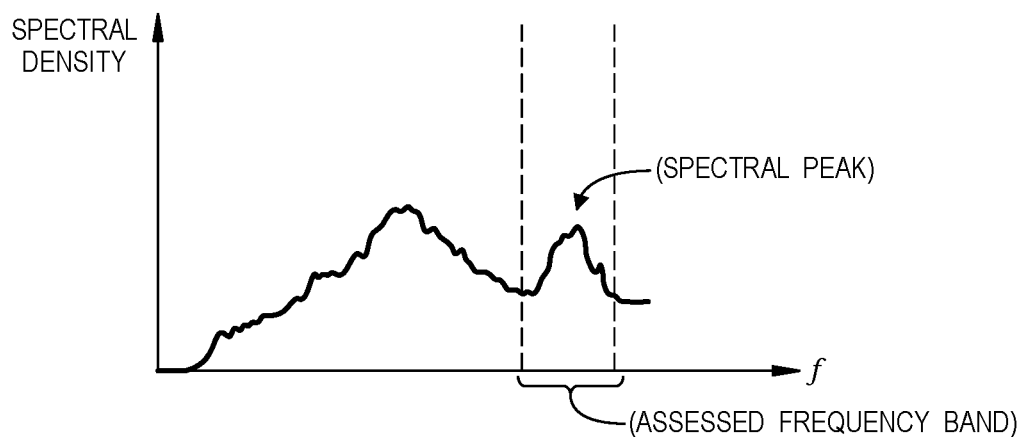

In another implementation, as shown in FIG. 3B, the system accesses a soundbite characterized by a spectrum containing a spectral peak within the assessed frequency band. Thus, although the majority of the sound energy of the soundbite can be distributed outside of the assessed frequency band, the soundbite, as transmitted by the system, includes significant information content within the assessed frequency band.

Figure 3C:
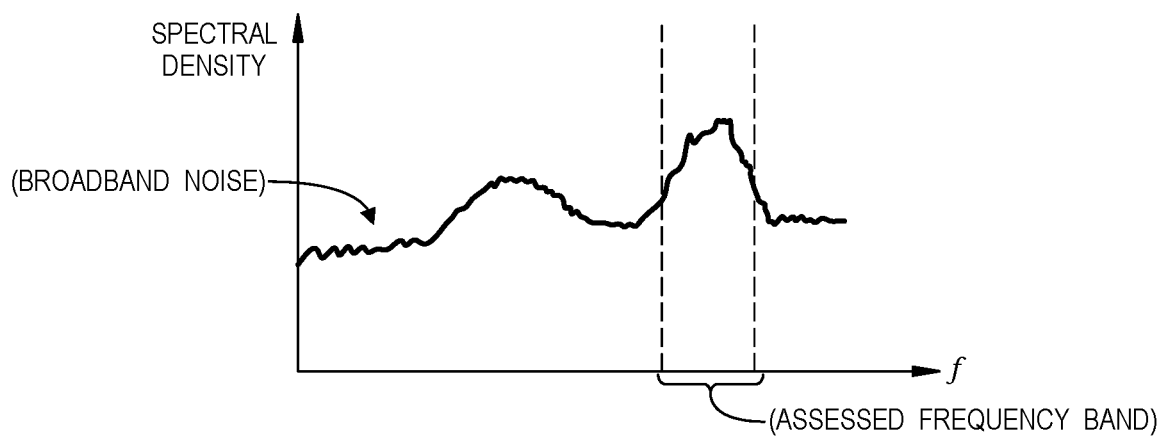

In yet another implementation, as shown in FIG. 3C, the system accesses a soundbite including a spoken phrase and broadband noise approximating typical environmental noise conditions. Thus, the soundbite can contain informational content within the assessed frequency band, which may be discerned from the broadband noise in order to comprehend the spoken phrase. In one variation, the system can record a noise sample of the testing environment (e.g., via a microphone integrated with the local computing device) and generate noise within the soundbite that, when combined with the recorded environmental noise, approximates an intended broadband noise profile.

In another variation, the system can playback soundbites during the hearing assessment process including specific types of background noise, such as background music, third party voices (e.g., as heard in a noisy restaurant), machinery, and/or other environmental noise that may affect the user's ability to hear voices. In this variation, the system can evaluate the user's hearing within different environmental conditions and generate desired hearing profiles for each environmental condition accordingly.

In yet another variation, the system can play back soundbites during the hearing assessment process that include specific recognizable, disruptive, and/or painful sounds such as an emergency siren, motorcycle engine, or any other sound, which may be concentrated within a particular frequency band. In this variation, the system can evaluate the user's sensitivity to loud sounds in order to generate a hearing profile that attenuates loud sounds within particular frequency bands.

For example, a user may express difficulty hearing or comprehending speech when occupying a crowded restaurant. As described above, the system can access a first soundbite including a spoken phrase and a sound clip of noise within an example crowded restaurant.

When accessing soundbites for an assessed frequency band, the system can access soundbites including particular phonemes, words, and narrators that transmit information necessary for comprehension within the assessed frequency band. When the soundbite includes a spoken phrase, the system can access soundbites including spoken phrases with specific phonemes that are characterized by spectra within the assessed frequency band. For example, the system can access a soundbite that includes several consonant phonemes spoken by a narrator that generates those phonemes within the assessed frequency band. In another example, the system can access a soundbite that includes several vowel phonemes characterized by formants within the assessed frequency band for the particular narrator.

Thus, the system can: access a first soundbite including a first spoken phrase characterized by a first frequency spectrum predominantly within a first frequency band in the set of frequency bands and narrated by a first narrator; and access a second soundbite including a second spoken phrase characterized by a second frequency spectrum predominantly within a second frequency band in the set of frequency bands different from the first frequency band and narrated by a second narrator.

Additionally, the system can: access a first soundbite including a first spoken phrase further including a first word characterized by a first frequency spectrum predominantly within a first frequency band in the set of frequency bands; and access a second soundbite including a second spoken phrase further including a second word characterized by a second frequency spectrum predominantly within a second frequency band in the set of frequency bands different from the first frequency band.

Alternatively, the system accesses soundbites including phonemically-balanced phrases such as "the boy was there when the sun rose" in order to assess a broader assessed frequency band.

When accessing soundbites for different assessed frequency bands, the system can access soundbites with different narrators, different phonemic content, different noise content depending on the implementation. For example, the system can access a first soundbite voiced by a male speaker when assessing a lower frequency band and access a second soundbite voiced by a female speaker for a higher frequency band.

Alternatively, the system can access the same soundbite for multiple frequency bands by applying a bandpass filter to attenuate frequency content of the soundbite outside of the assessed frequency band, thereby concentrating the spectral density of the soundbite within the assessed frequency band. In another alternative implementation, the system can modulate the frequency of the soundbite to shift the spectral peak and or spectral density of the soundbite from one frequency band to another. Thus, the system can assess multiple frequency bands while utilizing the same or a similar soundbite.

Therefore, the system can generate: the first soundbite by attenuating a first subset of the set of frequency bands of an initial soundbite, the first subset not including the first frequency band; and a second soundbite by attenuating a second subset of the set of frequency bands of the initial soundbite, the second subset not including a second frequency band different from the first frequency band.

In one implementation, the system can enable the user, via the user portal, to record a soundbite for incorporation in the hearing assessment process. For example, the user may decide to record the voice of a loved one such that the system executing the hearing assessment process adjusts the user's hearing profile to improve comprehension of the particular loved one.

In another implementation, the system can enable the user to initiate, via the user portal, a phone call while participating in the hearing assessment process such that the system executing the hearing assessment process can adjust the user's hearing profile to improve comprehension of the phone call. Therefore, instead of applying each test hearing profile to a prerecorded or synthesized soundbite the system can amplify, in real time, a phone call of the user with each hearing profile generated according to the hearing assessment process.

6.2 Hearing Profile Amplification

In Blocks S130 and S140, the system plays a soundbite amplified by a first gain in an assessed frequency band; and plays the soundbite amplified by a second gain in the assessed frequency band different from the first gain. More specifically, the system can apply a first test hearing profile and a second test hearing profile to a soundbite selected for evaluation of a user's preferred gain value in the assessed frequency band, wherein the difference between the first test hearing profile and the second test hearing profile is between the respective gain values of each profile within the assessed frequency band. Thus, the system is able to play, for the user, the same soundbite with different amplification within the same frequency band such that the user can form a preference between the two levels of amplification.

In Blocks S130 and S140, the system generates a first test hearing profile and a second test hearing profile based on the most recent hearing profile that the system has generated for the user being assessed. Initially, the system generates the first test hearing profile and the second test hearing profile based on the baseline hearing profile for the user. However, as the system received the user's preference regarding prior hearing profiles, the system can dynamically adjust the baseline hearing profile prior to initiating subsequent tests. Therefore, for each iteration of the hearing assessment process executed by the system, the system can generate and update the version of the hearing profile of the user. Thus, over multiple iterations of the hearing assessment process (i.e. Blocks S120, S130, S140, and S150) the system can transform the baseline hearing profile of the user by converging upon the refined (and more preferred) hearing profile for the user.

Figure 4A:
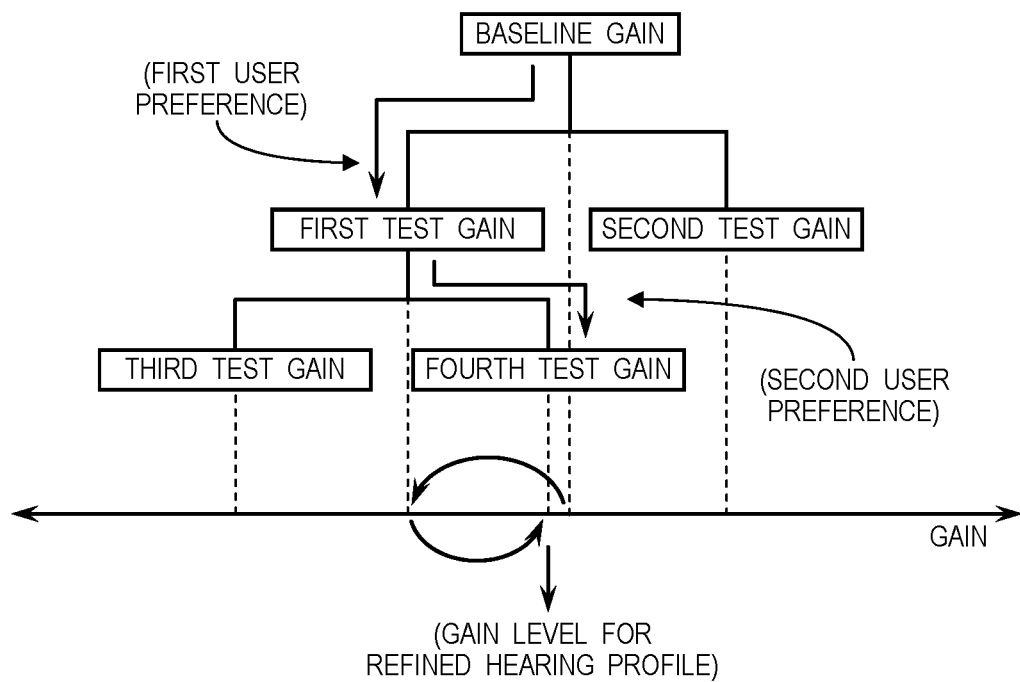
FIGS. 4A and 4B are flowchart representations of a variation of the method.

In one implementation, as shown in FIG. 4A, the system generates the first test hearing profile and the second test hearing profile according to a binary search algorithm, wherein an order relation (e.g., the ordering function) of the binary search algorithm is evaluated according to the user's preference between the two node profiles. Thus, the system can construct a preformed binary tree of gain levels for an assessed frequency band (with a predetermined leaf node resolution). The system can then locate the gain level in the binary tree equal to the current gain level in the assessed frequency band of the most recent hearing profile generated for the user. Alternatively, the system can generate a binary search tree that includes the baseline gain level in the assessed frequency band within the baseline hearing profile as the root node in the binary tree.

Once the system locates the current gain level for the user's hearing profile within the binary tree, the system can generate the first test hearing profile and the second test hearing profile by accessing the gain levels of the leaf nodes of the current gain level in the binary tree. Thus, the system sets the first gain level in the assessed frequency band of the first test hearing profile by referencing the first leaf node of the node representing the current gain level in the binary tree, while the system sets the second gain level in the assessed frequency band of the second test hearing profile by referencing the second leaf node of the node representing the current gain level in the binary tree. As a result, the system generates one test hearing profile with a gain level greater than the current gain level in the assessed frequency band while the system generates a second test hearing profile with a gain level less than the current gain level. However, when generating the test hearing profiles, the system keeps gain levels of the current hearing profile outside of the assessed frequency band consistent in order to provide a clear contrast to the user within the assessed frequency band. Thus, in one implementation, each hearing profile is identical except within the assessed frequency band.

Figure 4B:
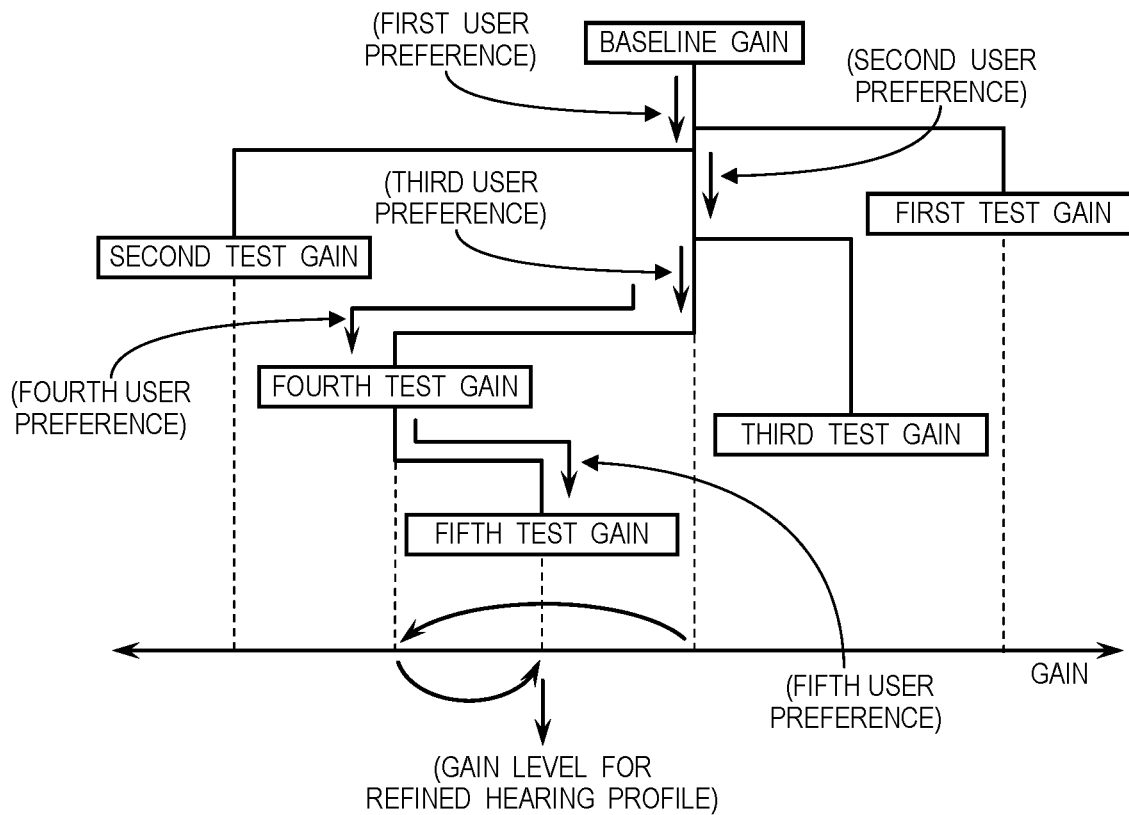

In one implementation, as shown in FIG. 4B, the system performs an A/B test procedure, wherein the system generates a single test hearing profile for comparison against the current hearing profile for the user. In this implementation, the system can alternate between generating test hearing profiles with a lower gain than the current hearing profile within the assessed frequency band and generating test hearing profiles with a higher gain than the current hearing profile with the assessed frequency band. Upon receiving a preference input from a user indicating a preference for the test hearing profile, the system can set the test hearing profile as the new current hearing profile. Upon receiving a preference input from a user indicating a preference for the current hearing profile, the system can reduce the difference in gain level in the assessed frequency band between the gain level of the current hearing profile and the gain level of each test hearing profile and play the soundbite amplified by two more test hearing profiles (one with a higher gain and one with a lower gain) for the user to evaluate against the current hearing profile. In this manner, the system can continually narrow the range of acceptable gain levels for the user until the user is satisfied with the current gain level of the current hearing profile in the assessed frequency band.

Upon receiving a repeated preference input (e.g., greater than a threshold number of preference inputs) for a current hearing profile, the system can cease the hearing assessment process for the assessed frequency band and select the current gain level as the gain level of the refined hearing profile for the assessed frequency band.

Once the system has generated each of the test hearing profiles for comparison by the user, the system can apply the hearing profiles to the soundbite selected for the assessed frequency band, thereby selectively amplifying frequency bands of the soundbite according to the gain values included in each hearing profile. The system can then play an output audio signal via speakers integrated with the local computing device or through electronically or wirelessly coupled speakers (e.g., headphones, earphones, or auxiliary speakers) such that both the first test soundbite and the second test soundbite (respectively amplified by the first and second test hearing profiles) are audible to the user.

6.3 User Feedback

In Block S150, the system can then prompt the user to input a preference for one of the test soundbites (e.g., from a set including a soundbite amplified according to the first test hearing profile and a soundbite amplified according to the second test hearing profile). The system can prompt the user to indicate which of the test soundbites is more audible to the user, and/or which enables the user to comprehend spoken words more clearly. For example, the system can: render—on a display of the computing device—the first test hearing profile applied to the first test soundbite and a second test hearing profile applied to the second test soundbite; prompt the user to select one of the two hearing profiles to indicate her preference for the first test soundbite or the second test soundbite; and then log the user's selection in a local and/or remote database.

In implementations wherein the system executes the hearing assessment process according to the above-described binary search algorithm, the system can update the current hearing profile of the user to match the test hearing profile corresponding to the test soundbite for which the user expressed a preference, thereby descending the binary search tree with each iteration of the hearing assessment process. In a subsequent iteration of the hearing assessment process, the system can then generate two additional test hearing profiles based on the leaf nodes of the new current node in the binary search tree.

In one variation, the system continues executing iterations of the hearing assessment process (i.e. Blocks S130, S140, and S150), according to the binary search algorithm until the system receives a preference of the user for a node with no leaf nodes, thereby ending the hearing assessment process for the assessed frequency band. However, the system can execute the hearing assessment process for other frequency bands in the set of frequency bands spanning the human-audible frequency range.

In implementations wherein the system executes the hearing assessment process according to the above-described A/B testing procedure, the system can update the current hearing profile of the user to match the test hearing profile upon receiving a user preference for the soundbite amplified according to the test hearing profile (as opposed to a user preference for the current hearing profile). If the system receives repeated preferences from the user for the current hearing profile, then the system can cease executing the hearing assessment test for the assessed frequency.

Thus, the system can: based on a first preference input representing a user's preference for a soundbite amplified by a second gain in the frequency band, as opposed to the soundbite amplified by a first gain in the frequency band: play the first soundbite amplified by a third gain in the first frequency band different from the first gain and the second gain, wherein the third gain is based on the second gain; play the first soundbite amplified by a fourth gain in the first frequency band different from the first gain, the second gain, and the third gain, wherein the fourth gain is based on the second gain; and receive a second preference input representing the user's preference from amongst the first soundbite amplified by the third gain in the first frequency band and the first soundbite amplified by the fourth gain in the first frequency band; and modify the first gain value corresponding to the first frequency band of the baseline hearing profile for the user based on the second preference input to generate the first refined hearing profile.

6.4 Frequency Band Selection

In order to execute multiple iterations of the hearing assessment process to identify the user's preferred gain level in each frequency band, the system selects an order of frequency bands with which to assess the preferred gain level of the user.

In one implementation, the system executes the hearing assessment process on each frequency band in the set of frequency bands in ascending order (with respect to the center frequency of each frequency band). Alternatively, the system executes the hearing assessment process on each frequency band in the set of frequency bands in descending order).

In another implementation, the system identifies a first frequency band for assessment based on the demographic data provided by the user in order to estimate the baseline hearing profile for the user. Alternatively, the system can estimate the type of hearing deficiency exhibited by the user (e.g., according to the hearing test model) and select, as the first frequency bands for assessment, the specific frequency bands in which the user is likely to exhibit greater hearing deficiency. Additionally, the system can define an order of assessment for the frequency bands in the set of frequency bands based on the demographic data provided by the user. For example, the system can prioritize the frequency bands in which hearing deficiency is frequently observed in users characterized by similar demographic data. Furthermore, the system can select an order of assessment for the frequency bands based on the baseline hearing profile of the user such that the frequency bands that correspond to the highest gain levels are assessed first, while frequency bands with lower gain levels are assessed later.

In yet another implementation, the system can prompt the user to select a frequency band for which the user desires further refinement in the amplification provided by the current hearing profile of the user. Thus, the system provides a means for the user to continue the hearing assessment process until the user is satisfied with her current hearing profile.

In one variation, the system can also selectively define frequency bands with a smaller bandwidth (frequency subbands) upon detecting a difference in the gain values of adjacent frequency bands. For example, upon detecting a difference above a threshold difference (e.g., 20 dB) between adjacent frequency bands, the system can define an additional frequency band in the hearing profile that has a center frequency between the center frequencies of the adjacent frequency bands. Furthermore, the system can modify the bandwidths of the adjacent frequency bands such that they do not overlap with the additional frequency band. The system can then estimate a baseline gain value for the additional frequency band such as by interpolating the gain values of the adjacent frequency bands.

6.5 Individual Ear Assessment

Furthermore, the system can implement each of the foregoing Blocks of the method S100 to individually assess hearing deficiency in each of the user's ears. For example, the system can output the first test soundbite and the second test soundbite through a left headphone and prompt the user to select which of the first test soundbite and the second test soundbite the user prefers in her left ear. The system can then output the first soundbite and the second soundbite through a right headphone and prompt the user to select which of the first test soundbite and the second test soundbite the user prefers in her right ear. As another example, the system can independently upload a left hearing profile to a left hearing device (or a right hearing profile to a right hearing device) such that the output of the left hearing device corresponds to the hearing profile being assessed and the output of the right hearing device is not augmented by a hearing profile (or vice versa). The system can also play a soundbite with one hearing profile on the left hearing device and the same soundbite with a second hearing profile on the left hearing device and prompt the user to select which of the hearing profiles the user prefers in her left ear. Additionally, the system can also assess both ears of the user together according to the method S100 if the system determines that the user's hearing deficiency in both ears is similar.

6.6 Volume Dependent Assessment

In one implementation, the system can generate separate refined hearing profiles each corresponding to different ranges of input volumes (e.g., overall input volume or within each individual frequency band) in order to provide volume-specific frequency response capabilities to the hearing assistance device. For example, a user (e.g., a construction worker or other user exposed to loud noises in the workplace) may wish to decrease volume of loud noises of specific frequencies (that are common on a construction site or that of a fire truck siren) and increase the relative volume of speech in order to hear speech through loud environmental background noise.

In particular, the system can generate a curve representing preferred gain levels for each assessed frequency band across the set of frequency bands and for each discrete range of input volumes, such as: input at normal speech volume; input at uncomfortably-loud volumes; and input at other volumes (e.g., whispers, etc.). The system can, therefore, execute the above-described Blocks of the method S100 at each input volume in order to determine the preferred gain values for each frequency band in the set of frequency bands and for each range of input volumes.

The system can also enable the user to manually adjust discrete points of the curve—such as corresponding to whispers (20-30 dB), normal speaking voice (60-70 dB) loud noises such as construction drills or jackhammers (greater than 90 dB)—to adjust the volume of singular frequencies or sub-ranges of frequencies within the audible range.

6.7 Refined Hearing Profile

As the system executes multiple iterations of the hearing assessment over a set of frequency bands, the system refines the baseline hearing profile of the user until the process is complete (as described above) and/or the user indicates that she is satisfied with the current hearing profile. The system can then record the current hearing profile of the user as the refined hearing profile of the user or generate the refined hearing profile for the user in Block S160.

However, the system can aggregate the user's feedback into a hearing profile in any other way such that, when applied to an input audio signal, a signal processor implementing the hearing profile increases amplitudes of select frequencies (or frequency bands) which the user indicated—during the hearing assessment—improved the user's comprehension of human speech. The system can therefore generate a custom hearing profile for the user (or for each of her ears) that represents the user's preferred amplification of particular frequencies across the audible spectrum.

The system can then store this custom hearing profile in the user's profile, such as in a remote database.

7. Hearing Assistance Device Need Assessment

The system can then determine whether the user may benefit from hearing aids. In particular, the system can determine whether: the user's hearing deficiency justifies the use of hearing aids by the user; the user's hearing abilities indicate no need for hearing augmentation; or whether the user's hearing deficiency may require more in-depth assessment by a doctor or audiologist.

In one implementation, if the refined hearing profile generated for the user deviates from a nominal hearing profile—associated with "normal" or fully-able hearing—by a first threshold difference (e.g., more than ten decibels at any frequency), the system can: determine that the user may benefit from hearing augmentation; present a visual representation of the refined hearing profile, such as in comparison to the nominal hearing profile, in order to visually communicate the user's hearing deficiency to the user; and prompt the user to order a hearing assistance device that best compensates for the user's hearing deficiencies and use cases. The system can then submit an order for a hearing assistance device to be delivered directly to the user in response to confirmation from the user.

However, in the foregoing example, if the refined hearing profile generated for the user deviates from the nominal hearing profile by more than a second threshold difference (e.g., more than 50 decibels at any frequency), the system can: flag the user as possibly exhibiting more-severe hearing deficiency; and prompt the user to visit a doctor, audiologist, or other professional for an in-person hearing assessment.

However, in response to the refined hearing profile aligning with the hearing profile of a user with normal hearing and/or deviating from the hearing profile of the user with normal hearing by less than a threshold deviation (e.g., five decibels), the system can notify the user that she exhibits little or no hearing deficiency and, therefore, may not require sound amplification.

Additionally, the system can compare the user's refined hearing profile to template hearing profiles indicating specific types of hearing deficiency (e.g., low-frequency hearing deficiency, cookie bite hearing deficiency, and/or noise-induced hearing deficiency) and, based on the comparison (e.g., if the refined hearing profile is within a threshold deviation of the template hearing profile), the system can prompt the user to order a specific hearing assistance device optimized for a type of hearing deficiency corresponding to the template hearing profile.

Additionally, the system can screen for contraindications that suggest that even if the user has a hearing deficiency and is in-range, she might still not benefit from hearing aids. For example, if the system determines that the left ear has a specific type of hearing deficiency and the right ear does not have significant hearing deficiency, the system can indicate that the user may have earwax blockage or an infection in the left ear that does not affect the right ear. As another example, the system can prompt the user to provide answers to a series of questions that screen for particular contraindications (e.g., an earwax blockage or ear infection).

Furthermore, the system can aid the user in determining whether she is in need of a hearing assistance device by playing a soundbite amplified according to the user's refined hearing profile and subsequently playing the soundbite without amplification (or vice versa). The system can then prompt the user to order a hearing assistance device if she perceives an improvement in the amplified soundbite when compared to the soundbite without amplification.

8. Configuration of the Hearing-Assistance Device

Upon receipt of a hearing assistance device (e.g., delivered hours, days, or weeks later), the user may pair the hearing assistance device to her computing device, such as over a local ad hoc wireless network. The system—executing on the user's computing device—can then: link the hearing assistance device (e.g., a unique identifier of the hearing assistance device) to the user's profile; retrieve the refined hearing profile generated during the initial assessment described above; and upload the refined hearing profile to the hearing assistance device.

The hearing assistance device can then immediately begin: detecting audio signals in; processing these audio signals according to the refined hearing profile; and outputting these processed audio signals—now with select frequency bands amplified according to the refined hearing profile—via a speaker integrated into the hearing assistance device. The hearing assistance device can therefore implement the refined hearing profile generated during the hearing assessment, which was performed on the user's computing device with another audio output device (e.g., a separate set of headphones).

However, because the hearing assistance device may (or is likely) to exhibit an frequency response that differs from the frequency response of the user's computing device and headphones, the refined hearing profile generated during the hearing assessment may fully compensate for the user's hearing loss when implemented by the hearing assistance device. Nonetheless, the refined hearing profile generated during the hearing assessment may better represent the user's hearing augmentation needs than a nominal hearing profile when implemented by the hearing assistance device. Therefore, the hearing assistance device can initially implement the refined hearing profile; and the system can cooperate with the hearing assistance device to execute an on-device hearing assessment and to modify the refined hearing profile accordingly.

In one implementation, the system can also configure the hearing device with automatic feedback cancellation to prevent the hearing assistance device from entering a feedback amplification loop. In this implementation, the system can play load noise and subsequently prompt the user to indicate whether she perceived any feedback from the hearing assistance device. In response to a positive response, the system can then modify feedback cancellation settings of the hearing assistance device.

8.1 On-Device Hearing Assessment

Generally, as shown in FIG. 2, the hearing assistance device and the system can cooperate: to test effectiveness of the refined hearing profile in improving the user's comprehension of human speech when implemented by the hearing assistance device (rather than the user's computing device and headphones); and to adjust the refined hearing profile for implementation by the hearing assistance device given the user's feedback of A/B audio tests performed with the hearing assistance device. The system can continue to asses, via the A/B assessment process or binary tree assessment, the user's preferences for the gain levels of the refined hearing profile when replayed through the hearing assistance device and to converge on a revised hearing profile for implementation by the hearing assistance device accordingly.

More specifically, the system can: access a refined hearing profile of a user in Block S170; upload the revised hearing profile to the hearing assistance device in Block S180; at a first time, in response to receiving a confirmation of activation of the refined hearing profile from the hearing assistance device, play a soundbite corresponding to a assessed frequency band in Block S190; access a revised hearing profile of the user in Block S172; upload the revised hearing profile to the hearing assistance device in Block S182; at a second time succeeding the first time and in response to receiving a confirmation of activation of the revised hearing profile from the hearing assistance device, replaying the first soundbite in Block S192; in response to receiving a first preference input representing a preference of the user for the revised hearing profile, select the revised hearing profile in Block S194; and prompt the hearing assistance device to set the revised hearing profile as an active hearing profile for the hearing assistance device in Block S196.

In one variation, after uploading the refined hearing profile—generated during the initial assessment as described above—to the hearing assistance device and once the user initiates an on-device hearing assessment, the system can execute a process for revising the refined hearing profile similar to the hearing assessment process described above. However, instead of selectively amplifying each soundbite based on test hearing profiles, the system can: upload the test hearing profiles to the hearing assistance device; confirm that the hearing assistance device has activated the hearing profile (e.g., the digital signal processor of the hearing device is executing a set of digital filter in order to amplify input sound according to the uploaded hearing profile); and play the raw soundbite (e.g., without amplification) such that the only amplification applied to the soundbite is performed at the hearing assistance device. Thus, the system can assess user preferences for the refined hearing profile given the particular frequency response characteristics of the hearing assistance device.

The system can generate test hearing profiles in the same manner as described above with respect to the hearing assessment process; and receive feedback from the user in the same manner (e.g., via the user portal). Thus, when executing the on-device hearing assessment the system executes Blocks S170, S172, S180, S182, S190, S192, S194, and S196 to converge from the refined hearing profile to a revised hearing profile better optimized for the particular hearing assistance device.

Furthermore, the system can execute on-device testing for any other sound generating device, such as a telephone, speaker system, or computational device with integrated speakers. Because each hearing profile indicates a frequency response profile over a set of frequency bands, the system can transfer hearing profiles to any device with a digital signal processor capable of applying the hearing profile to an input audio signals to generate amplified output audio signals.

8.2 Telephone Hearing Assessment

In one implementation, the system can: initiate a phone call for the user, the phone call amplified according to the user's refined hearing profile; receive feedback from the user describing the clarity of the phone call; amplify the phone call according to a revised hearing profile characterized by a second gain value corresponding to the first frequency band; receive a second preference input representing a preference of the user for the revised hearing profile; and upload the revised hearing profile to a hearing assistance device. Thus, the system can perform the on-device hearing assessment described above utilizing the user's telephone instead of a hearing assistance device.

8.3 Revised Hearing profile

In Block S196, the system can, in response to selection of the second soundbite, generate a revised hearing profile for the user representing amplification of the subset of frequencies to the second gain level. Generally, in Block S196, the system can modify the refined hearing profile (or generate a revised hearing profile) that represents a user's preference for sound augmentation by the hearing assistance device(s) across the audible spectrum or, more specifically, across the vocal spectrum.

In one implementation, the system records gain level differences in discrete frequencies or frequency bands of hearing profiles for which the user indicated a preference over other soundbites not exhibiting gain level changes over such discrete frequencies or frequency ranges. The system can then interpolate between the gain levels changes across the audible or vocal spectrum to generate the revised refined hearing profile for the user.

9. Examples

In one example, the user enters—during the on-device hearing assessment—a preference for amplification of sounds at 500 Hz by ten decibels, sounds at 1 k Hz by five decibels, sounds at 2 k Hz by three decibels, sounds at 4 k Hz by two decibels, and sounds at 6 k Hz by five decibels. (The system can also interpolate preferences for gain level changes at frequencies between each of the frequencies tested during the on-device hearing assessment (e.g., 750 Hz, 1.5 k Hz, 3 k Hz, and 5 k Hz). Upon conclusion of the on-device hearing assessment (or throughout the on-device hearing assessment), the system can then: calculate a curve using audio filters (peaking equalizer filters and compression filters)—across the audible or vocal spectrum—that best fits these gain level change preferences indicated by the user at the discrete frequencies and store this equalizer curve as a new refined hearing profile for the user; and upload the new refined hearing profile to the user's hearing aid(s).

In the foregoing example, the system can increase volume of the amplitude of a narrow frequency range containing the "eff" phoneme by three decibels in the second soundbite compared to the first soundbite. The hearing assistance device can then: process and output the first soundbite according to the refined hearing profile; and process and output the second soundbite according to the refined hearing profile after completion of playback of the first soundbite. The computing device can then prompt the user to select which of the first soundbite and the second soundbite the user prefers or can hear more clearly. In the foregoing example, if the "ess" phoneme in "The boy was there when the sun rose" is clear in the first soundbite but too loud in the second soundbite, the user can indicate a preference for the first soundbite in the user portal; the system can thus determine that the custom original hearing profile is better tuned to the user's hearing ability in the narrow frequency range containing the "ess" phoneme than the modified refined hearing profile and confirm no change in this narrow frequency range in the refined hearing profile. However, if the "ess" phoneme in "The boy was there when the sun rose" is too quiet in the first soundbite and at a more comfortable volume for the user in the second soundbite, the user can indicate a preference for the second soundbite in the user portal; the system can thus determine that the modified refined hearing profile is better tuned to the user's hearing ability in the narrow frequency range containing the "ess" phoneme than the original refined hearing profile and then update the refined hearing profile for the user to reflect this preference for increased amplitude within the narrow frequency range containing the "ess" phoneme accordingly.

In the foregoing example, if the user indicates a preference for the first soundbite, the system can also: generate a third soundbite including the soundbite with the volume in the narrow frequency range containing the "ess" phoneme decreased by three decibels; upload the third sound amplification profile to the hearing assistance device; and present the third soundbite to the user. The hearing assistance device can then replay the first and third soundbites in quick succession, and the system can prompt the user to select which of the first and third soundbites she prefers or can comprehend more clearly. The system can then update the refined hearing profile accordingly.

In another example, a computing device, such as a smartphone, can present or play the first soundbite and the second soundbite at a default volume (e.g., a volume corresponding to a volume of normal human speech). In this example, the hearing assistance device's microphone can record or process the soundbites according to the sound amplification profile and output the soundbite into the user's ear according to the custom sound amplification profile for the user. Therefore, the hearing assistance device can locally modify sound presented to the user while the computing device plays a standard, unmodified soundbite.

In another example, the system can increase volumes of discrete frequency ranges (e.g., by 10 decibels) in discrete intervals (e.g., every 50 Hz) across the audible spectrum or across the vocal spectrum in a series of soundbites and upload original and modified versions of these soundbites to the hearing assistance device. The hearing assistance device can then process original and modified versions of these soundbites according to the refined hearing profile currently stored on the hearing assistance device when replaying these soundbites for the user. In a similar example, the system and the hearing assistance device can cooperate: to playback a first soundbite containing an soundbite in which a volume of a first frequency (e.g., 20 Hz) is played back at a default volume; to playback a second soundbite containing the soundbite with the first frequency amplified by five decibels; and to prompt the user to indicate which of the first and the second soundbites she prefers (or which is more comprehensive or "sounds better"). The system and the hearing assistance device can then cooperate: to playback a third soundbite containing a second soundbite in which a second frequency (e.g., 70 Hz) is played back at a default volume; to playback a fourth soundbite containing the second soundbite with the second frequency amplified by five decibels; and to prompt the user to indicate which of the third and the fourth soundbites she prefers. The system can then update the refined hearing profile for the user accordingly.

However, the system can cooperate with the hearing assistance device in any other way: to test changes in single frequencies, discrete ranges of frequencies, groups of discrete frequencies, etc. in the audible spectrum (e.g., 20-20,000 Hz) and/or in the vocal spectrum (e.g., 125-8,000 Hz) during this on-device hearing assessment; and to modify the refined hearing profile based on the user's feedback during the on-device hearing assessment.

10. Customization

In one variation, the system can prompt the user to manually adjust gain level settings of select frequencies, such as through an interface rendered within the system. In this variation, the system can render an interface including slider icons that the user may toggle to manually increase and/or decrease the gain level of a particular frequency. The system can render a set of sliders configured to increase and/or decrease the gain level of a subset of frequencies—distributed at intervals across a spectrum of frequencies (e.g., between 125 Hz and 8,000 Hz)—in response to input by the user.

Additionally or alternatively, the system can render a representation of the refined hearing profile (e.g., a graph with a first axis representing a range of frequencies and a second axis representing a gain level or amplitude) currently loaded onto the user's hearing aid(s).

For example, the system can render a curve representing preferred gain level settings for each tested frequency across the range of frequencies and can enable the user to manually adjust discrete points of the curve to adjust the gain level of frequencies within the range of frequencies. Upon completion of each manual adjustment of the refined hearing profile through the system by a user, the system can upload this revised refined hearing profile to the hearing aid, and the hearing aid can implement this revised refined hearing profile until a new hearing profile is loaded onto the hearing aid.

Furthermore, the system can render a selection of commonly voiced sounds, such as consonant sounds (e.g., "F", or "S"), vowels (e.g., "ah," or "ee"), words (e.g., "the," "with,"), etc. The system can then prompt the user to toggle a gain level amplification slider (or switch) to increase and/or decrease the gain level at which these (or a subset of these) commonly voiced sounds are played back by the hearing aid. Additionally or alternatively, the system can query the user to enter whether she experiences difficulty hearing these (or a subset of these) commonly voiced sounds, whether she prefers amplification of these (or a subset of these) commonly voiced sounds, etc. The system can then update the sound amplification assigned to the user profile accordingly.

11. Hearing Profile Reassessment

The system can prompt the user to reassess her hearing periodically (e.g., every week, every month, every six months, etc.) to confirm that the refined hearing profile currently implemented by the hearing aid reflects the user's current sound preferences or hearing augmentation needs. During these additional hearing assessments the system can cooperate with the hearing aid to collect sound augmentation preferences from the user and to modify the refined hearing profile for the user accordingly. The system can then upload the new refined hearing profile to the hearing aid for immediate implementation or the shift hearing aid from its current refined hearing profile to the new refined hearing profile over a period of time (e.g., over a period of two weeks) to enable the user to gradually grow accustomed to the new customer hearing profile.

The system and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for evaluating hearing of a user comprising:
generating a baseline hearing profile for the user comprising a set of gain values based on a first volume setting, each gain value in the set of gain values corresponding to a frequency band in a set of frequency bands spanning a human-audible frequency range;
accessing a first soundbite comprising a first spoken phrase characterized by a first frequency spectrum predominantly within a first frequency band in the set of frequency bands;
playing the first soundbite amplified by a first gain in the first frequency band;
playing the first soundbite amplified by a second gain in the first frequency band different from the first gain;
receiving a first preference input representing a preference of the user from amongst the first soundbite amplified by the first gain in the first frequency band and the first soundbite amplified by the second gain in the first frequency band; and
modifying a first gain value, corresponding to the first frequency band, in the baseline hearing profile based on the first preference input to generate a first refined hearing profile compensating for hearing deficiency of the user.

2. The method of claim 1 further comprising uploading, to a hearing assistance device the first refined hearing profile.

3. The method of claim 2 further comprising:
at a first time and in response to receiving a confirmation of activation of the first refined hearing profile from the hearing assistance device, playing the second soundbite;
uploading a second refined hearing profile to the hearing assistance device, the second refined hearing profile comprising a second set of gain values, each gain value in the second set of gain values corresponding to a frequency band in the set of frequency bands and characterized by a second gain value in the second set of gain values corresponding to the first frequency band;
at a second time succeeding the first time and in response to receiving a confirmation of activation of the second refined hearing profile from the hearing assistance device, replaying the second soundbite;
in response to receiving a second preference input representing a preference of the user for the second refined hearing profile, selecting the second refined hearing profile; and
prompting the hearing assistance device to set the second refined hearing profile as an active hearing profile for the hearing assistance device.

4. The method of claim 1 further comprising, in response to the first refined hearing profile deviating from a nominal hearing profile greater than a threshold deviation, prompting the user to obtain a hearing assistance device.

5. The method of claim 1:
further comprising receiving the first volume setting, the first volume setting representing a minimum understandable volume at which the user can understand speech in a first exploratory soundbite, the first exploratory soundbite characterized by a first frequency; and
wherein generating the baseline hearing profile for the user further comprises generating the baseline hearing profile based on the first volume setting and a hearing profile model.

6. The method of claim 5, wherein receiving the first volume setting further comprises:
playing the first exploratory soundbite at an initial volume;
prompting the user to adjust the volume from the initial volume to the minimum understandable volume to the user; and
recording the minimum understandable volume to the user as the first volume setting.

7. The method of claim 5, further comprising:
receiving a second volume setting, the second volume setting representing a minimum understandable volume to the user of a second exploratory soundbite, the second exploratory soundbite characterized by a second frequency; and
wherein generating the baseline hearing profile for the user further comprises generating the baseline hearing profile based on the first volume setting, the second volume setting, and the hearing profile model.

8. The method of claim 1:
further comprising accessing demographic data of the user comprising at least one of:
an age of the user;
a sex of the user; and
an occupation of the user;
wherein generating the baseline hearing profile for the user further comprises generating the baseline hearing profile based on the demographic data and the hearing profile model.

9. The method of claim 8, further comprising selecting the first frequency band in the set of frequency bands based on the demographic data.

10. The method of claim 1, wherein accessing the first soundbite further comprises accessing the first soundbite comprising the first spoken phrase characterized by a spectral density within the first frequency band exceeding a threshold spectral density.

11. The method of claim 1, wherein accessing the first soundbite further comprises accessing the first soundbite comprising the first spoken phrase and broadband noise approximating typical environmental noise conditions.

12. The method of claim 1, wherein modifying the first gain value, corresponding to the first frequency band, in the baseline hearing profile further comprises:
based on the first preference input representing a preference of the user for the first soundbite amplified by the second gain in the first frequency band:
playing the first soundbite amplified by a third gain in the first frequency band different from the first gain and the second gain; and
playing the first soundbite amplified by a fourth gain in the first frequency band different from the first gain, the second gain, and the third gain;
receiving a second preference input representing the user's preference from amongst the first soundbite amplified by the third gain in the first frequency band and the first soundbite amplified by the fourth gain in the first frequency band; and
modifying the first gain value corresponding to the first frequency band of the baseline hearing profile for the user based on the second preference input to generate the first refined hearing profile.

13. The method of claim 1:
wherein accessing the first soundbite further comprises accessing the first soundbite comprising the first spoken phrase characterized by the first frequency spectrum and narrated by a first narrator; and
further comprising:
accessing a second soundbite comprising a second spoken phrase characterized by a second frequency spectrum predominantly within a second frequency band in the set of frequency bands different from the first frequency band and narrated by a second narrator;
playing a second soundbite amplified by a third gain in the second frequency band;
playing the second soundbite amplified by a fourth gain in the second frequency band, the fourth gain different from the third gain;
receiving a second preference input representing a preference of the user from amongst the second soundbite amplified by the third gain in the second frequency band and the second soundbite amplified by the fourth gain in the second frequency band; and
modifying a second gain value corresponding to the second frequency band of the first refined hearing profile based on the second preference input to generate a second refined hearing profile for the user.

14. The method of claim 1:
wherein accessing the first soundbite further comprises accessing the first soundbite comprising the first spoken phrase further comprising a first word characterized by the first frequency spectrum; and
further comprising:
accessing a second soundbite comprising a second spoken phrase further comprising a second word characterized by a second frequency spectrum predominantly within a second frequency band in the set of frequency bands different from the first frequency band;
playing the second soundbite amplified by a fourth gain in the second frequency band different from the third gain;
receiving a second preference input representing a preference of the user from amongst the second soundbite amplified by the third gain in the second frequency band and the second soundbite amplified by the fourth gain in the second frequency band; and
modifying a second gain value corresponding to the second frequency band of the first refined hearing profile for the user based on the second preference input to generate a second refined hearing profile.

15. The method of claim 1, further comprising:
generating the first soundbite by attenuating a first subset of the set of frequency bands of an initial soundbite, the first subset not including the first frequency band;
generating a second soundbite by attenuating a second subset of the set of frequency bands of the initial soundbite, the second subset not including a second frequency band different from the first frequency band;
playing the second soundbite amplified by a third gain in the second frequency band, the second soundbite comprising a second auditory phrase characterized by a second frequency spectrum predominantly within the second frequency band;
playing the second soundbite amplified by a fourth gain in the second frequency band, the fourth gain different from the third gain;
receiving a second preference input representing a preference of the user from amongst the second soundbite amplified by the third gain in the second frequency band and the second soundbite amplified by the fourth gain in the second frequency band; and
modifying the second frequency band of the first refined hearing profile for the user based on the second preference input to generate a second refined hearing profile.

16. The method of claim 1, further comprising:
selecting a second frequency band adjacent to the first frequency band in the set of frequency bands, the second frequency band characterized by a center frequency different than a center frequency of the first frequency band;
playing a second soundbite amplified by a third gain in the second frequency band, the second soundbite comprising a second auditory phrase characterized by a second frequency spectrum predominantly within the second frequency band;
playing the second soundbite amplified by a fourth gain in the second frequency band, the fourth gain different from the third gain;
receiving a second preference input representing a preference of the user from amongst the second soundbite amplified by the third gain in the second frequency band and the second soundbite amplified by the fourth gain in the second frequency band; and
modifying a second gain value corresponding to the second frequency band of the first refined hearing profile based on the second preference input to generate a second refined hearing profile for the user.

17. The method of claim 16, wherein selecting the second frequency band adjacent to the first frequency band in the set of frequency bands further comprises selecting the second frequency band based on a difference between the first gain value corresponding to the first frequency band in the first refined hearing profile and a third gain value corresponding to a third frequency band in the first refined hearing profile, the third frequency band adjacent to the second frequency band and not adjacent to the first frequency band.

18. The method of claim 1 further comprising:
initiating a phone call for the user, the phone call amplified according to the first refined hearing profile;
receiving feedback from the user describing the clarity of the phone call;
amplifying the phone call according to a second refined hearing profile characterized by a second gain value corresponding to the first frequency band;
receiving a second preference input representing a preference of the user for the second refined hearing profile;
uploading the second refined hearing profile to a hearing assistance device.

19. The method of claim 1:
wherein:
generating the baseline hearing profile for the user further comprises generating the baseline hearing profile for the user comprising the set of gain values corresponding to a first volume level and a second set of gain values corresponding to a second volume level greater than the first volume level, each gain value in the second set of gain values corresponding to a frequency band in the set of frequency bands;

playing the first soundbite amplified by the first gain further comprises playing the first soundbite amplified by the first gain in the first frequency band at a first volume; and playing the first soundbite amplified by the second gain in the first frequency band further comprises playing the first soundbite amplified by the second gain in the first frequency band at the first volume; and further comprising:

playing the first soundbite amplified by the first gain in the first frequency band at a second volume; and playing the first soundbite amplified by the second gain in the first frequency band at the second volume; and receiving a second preference input representing a preference of the user from amongst the first soundbite amplified by the first gain in the first frequency band at the second volume and the first soundbite amplified by the second gain in the first frequency band at the second volume; and modifying a first gain value in the second set of gain values corresponding to the first frequency band of the first refined hearing profile for the user based on the second preference input to generate a second refined hearing profile.

20. A method for adjusting a hearing assistance device comprising:

accessing a first hearing profile for a user comprising a first set of gain values, each gain value in the first set of gain values corresponding to a frequency band in a set of frequency bands spanning human audible range and characterized by a first gain value in the first set of gain values corresponding to a first frequency band;

uploading the first hearing profile to the hearing assistance device of the user;

at a first time and in response to receiving a confirmation of activation of the first hearing profile from the hearing assistance device, playing a first soundbite comprising a first spoken phrase characterized by a first frequency spectrum predominantly within the first frequency band;

accessing a second hearing profile for the user comprising a second set of gain values, each gain value in the second set of gain values corresponding to a frequency band in the set of frequency bands and characterized by a second gain value in the second set of gain values corresponding to a first frequency band;

uploading the second hearing profile to the hearing assistance device;

at a second time succeeding the first time and in response to receiving a confirmation of activation of the second hearing profile from the hearing assistance device, replaying the first soundbite;

in response to receiving a first preference input representing a preference of the user for the second hearing profile, selecting the second hearing profile; and prompting the hearing assistance device to set the second hearing profile as an active hearing profile for the hearing assistance device.

* * * * *